(12) United States Patent
Hays

(10) Patent No.: US 8,137,712 B2
(45) Date of Patent: Mar. 20, 2012

(54) REHYDRATION BEVERAGE

(75) Inventor: Evan Hays, Dallas, TX (US)

(73) Assignee: Evan Hays, Dallas, TX (US)

( * ) Notice: Subject to any disclaimer, the term of this patent is extended or adjusted under 35 U.S.C. 154(b) by 43 days.

(21) Appl. No.: 12/376,694

(22) PCT Filed: Aug. 8, 2007

(86) PCT No.: PCT/US2007/075440
§ 371 (c)(1),
(2), (4) Date: Feb. 6, 2009

(87) PCT Pub. No.: WO2008/021861
PCT Pub. Date: Feb. 21, 2008

(65) Prior Publication Data
US 2010/0183736 A1 Jul. 22, 2010

Related U.S. Application Data

(60) Provisional application No. 60/836,474, filed on Aug. 9, 2006.

(51) Int. Cl.
*A61K 36/25* (2006.01)
*A61K 36/906* (2006.01)
*A61K 36/00* (2006.01)

(52) U.S. Cl. .......... 424/728; 424/756; 424/725
(58) Field of Classification Search .......... None
See application file for complete search history.

(56) References Cited

U.S. PATENT DOCUMENTS

| | | | |
|---|---|---|---|
| 2003/0194746 A1* | 10/2003 | Petyaev | 435/7.1 |
| 2005/0031761 A1 | 2/2005 | Brucker et al. | |
| 2007/0124175 A1* | 5/2007 | Jung et al. | 705/3 |
| 2007/0196518 A1* | 8/2007 | Wojewnik et al. | 424/729 |
| 2007/0289258 A1* | 12/2007 | Jung et al. | 53/443 |

OTHER PUBLICATIONS

PROMT Abstract of Product Alert Bulletin entitled UnDo Herbal Supplement Tablets—Blended Fiber, Blended Herbs; natural Herb & Gentle Fiber Whole-Body Cleansing Program, Jul. 22, 1996.
International Search Report, United States Patent and Trademark Office, PCT/US2007/75440, dated Jan. 30, 2008.
Written Opinion of the International Searching Authority, United States Patent and Trademark Office, PCT/US2007/75440, dated Jan. 30, 2008.
International Preliminary Report on Patentability, PCT/US2007/75440, dated Feb. 10, 2009.

* cited by examiner

*Primary Examiner* — Christopher R. Tate
(74) *Attorney, Agent, or Firm* — Marshall, Gerstein & Borun LLP

(57) ABSTRACT

The present invention relates to a composition for the relief of hangover symptoms and methods of treating hangover symptoms.

3 Claims, No Drawings

REHYDRATION BEVERAGE

CROSS-REFERENCE TO RELATED APPLICATION

This application claims the benefit of priority to U.S. Provisional Application No. 60/836,474, filed Aug. 9, 2006, the disclosure of which is incorporated herein by reference in its entirety.

FIELD OF THE INVENTION

The present invention relates to a composition for the relief of hangover symptoms and methods of treating hangover symptoms.

BACKGROUND OF THE INVENTION

The ingestion of alcoholic beverages, even when consumed in moderation, may lead to a variety of post-consumption symptoms, including headache, tremulousness, nausea, sour stomach, diarrhea, dizziness, fatigue and decreased cognitive or visual-spatial skills, collectively and popularly known as "hangover."

Such symptoms are believed to be connected to dehydration, hormonal alterations, deregulation of cytokine pathways and a variety of other toxic effects of alcohol. Of these, dehydration is believed to be one of the primary causes of hangover symptoms. As an alcoholic beverage is ingested, ethanol is absorbed into the blood stream. In the body, ethanol and its metabolites are identified as toxins and broken down to less harmful chemical entities. The liver and kidneys are the organs where most of the toxin processing takes place. In order for toxins to be processed adequately by the liver and kidneys, they must be dissolved in water. When the amount of toxins generated by alcohol consumption is higher than the amount of water available in the stomach, water is drawn from other areas of the body, such as the blood, the lymph nodes and the brain, causing dehydration, which in turn may result in effects ranging from mere headaches to serious harm to the brain, kidneys, liver, lymph nodes and other vital organs of the body, up to and including death.

Another toxic effect of alcohol consumption is associated with the buildup of acetaldehyde during the metabolism of ethanol by the liver and kidneys. Ethanol breakdown in the liver involves two steps which are catalyzed by two different enzymes. In the first step, the enzyme alcohol dehydrogenase converts ethanol in to acetaldehyde, which is toxic. In the second step, the enzyme dehydrogenease converts the acetaldehyde into harmless acetate. When acetaldehyde is produced at a faster rate than it is converted to acetate, excess acetaldehyde accumulates in the liver, causing severe toxic effects, up to and including breakdown of liver tissue.

Many attempts have been made to devise remedies to alleviate the many symptoms of hangover, but very few are effective against the large variety of symptoms noted above. In addition, many over-the-counter remedies have their own deleterious side effects. There is therefore a need for a composition for broad spectrum relief from the many symptoms of hangover that is safe and effective.

SUMMARY OF THE INVENTION

The present invention provides a formulation for the relief of hangover symptoms. A hangover is characterized by the constellation of unpleasant physical and mental symptoms that occur after a bout of heavy alcohol drinking. Physical symptoms of a hangover include fatigue, headache, increased sensitivity to light and sound, redness of the eyes, muscle aches, and thirst. Signs of increased sympathetic nervous system activity can accompany a hangover, including increased systolic blood pressure, rapid heartbeat (i.e., tachycardia), tremor, and sweating. Other symptoms include dizziness; a sense of the room spinning (i.e., vertigo); and possible cognitive and mood disturbances, especially depression, anxiety, and irritability.

In one embodiment, the formulation is a composition comprising at least two different components selected from the group consisting of milk thistle extract, ginseng extract and ginger root extract. In a related embodiment, the composition comprises, when present in an 8 oz. volume, at least two different components selected from the group consisting of milk thistle extract, ginseng extract and ginger root extract, is included in amounts ranging from about 2 mg to about 2 g. In one aspect, the composition is an aqueous composition.

In another embodiment, the formulation is a composition comprising milk thistle extract, ginseng extract and ginger root extract, when present in an 8 oz. volume, are included in amounts ranging from about 2 mg to about 2 g.

In another embodiment, a composition of the invention is provided further comprising at least one electrolyte selected from the group consisting of salts of a metal ion of Groups I and II of the periodic table. In various aspects, suitable electrolytes include, but are not limited to sodium acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulfate (anhydrous), sodium sulphate (Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulfate. In one aspect, a composition of the invention is provided further comprising, when present in an 8 oz. volume, sodium chloride is included in an amount ranging from about 50 mg to about 500 mg, monopotassium phosphate is included in an amount ranging from about 10 mg to about 200 mg and magnesium sulfate is included in an amount ranging from about 10 mg to about 200 mg.

In yet another embodiment, a composition of the invention is provided further comprising at least one carbohydrate selected from the group consisting of a monosaccharide, a disaccharide, an oligosaccharide and a glucose polymer.

In another embodiment, a composition of the invention is provided further comprising one or more vitamins of the vitamin B group selected from the group consisting of vitamin B1 (thiamin), vitamin B2 (riboflavin), vitamin B3 (niacin), vitamin B5 (pantothenoic acid or calcium pantothenate), vitamin B6 and vitamin B12. In one aspect, the composition comprises, when present in an 8 oz. volume, vitamin B1 (thiamin) is included in an amount ranging from about 0.1 mg to about 5 mg, vitamin B2 (riboflavin) is included in an amount ranging from about 0.1 mg to about 5 mg, vitamin B3 (niacin) is included in an amount ranging from about 1 mg to about 50 mg, vitamin B5 (pantothenoic acid) is included in an amount ranging from about 1 mg to about 50 mg, vitamin B6 is included in an amount ranging from about 0.1 mg to about 5 mg, and vitamin B12 is included in an amount ranging from about 1 μg to about 50 μg.

In yet another embodiment, a composition of the invention is provided further comprising vitamin A, when present in an 8 oz. volume, is included in an amount ranging from about 50 IU to about 1000 IU.

In another embodiment, the aforementioned composition is provided further comprising, further comprising vitamin C, when present in an 8 oz. volume, is included in an amount ranging from about 10 mg to about 100 mg.

In another embodiment, a composition of the invention is provided further comprising vitamin E, when present in an 8 oz. volume, is included in an amount ranging from about 1 IU to about 50 IU.

In yet another embodiment, a composition of the invention is provided further comprising one or more amino acids selected from the group consisting of alanine, arginine, creatine, cysteine, glutamine, histidine, lysine, methionine, ornithine, leucine, isoleucine, tryptophan, valine, and phenylalanine. In one aspect, a composition of the invention is provided further comprising cysteine and glutamine, when present in an 8 oz. volume, is included in an amount ranging from about 10 mg to about 100 mg, respectively.

In still another embodiment, a composition of the invention is provided comprising, when present in an 8 oz. volume, 50 mg milk thistle extract, 50 mg ginseng extract, 50 mg ginger root extract, 25 mg fructose, 110 mg sodium chloride, 30 mg monopotassium phosphate, 30 mg magnesium sulfate, 50 mg cysteine, 5 mg glutamine, 2.1 µg vitamin B12, 0.7 mg vitamin B6, 3.5 mg vitamin B5, 0.525 mg vitamin B1, 7 mg vitamin B3, 0.6 mg vitamin B2, 60 mg vitamin C, 500 IU vitamin A, 3 IU vitamin E.

In still another embodiment, a composition of the invention is provided comprising, when present in an 8 oz. volume, 50 mg milk thistle extract, 50 mg ginseng extract, 50 mg ginger root extract, 25 mg fructose, 110 mg sodium chloride, 30 mg monopotassium phosphate, 30 mg magnesium sulfate, 50 mg cysteine, 20 mg glutamine, 2.1 µg vitamin B12, 0.7 mg vitamin B6, 3.5 mg vitamin B5, 0.525 mg vitamin B1, 7 mg vitamin B3, 0.6 mg vitamin B2, 60 mg vitamin C, 500 IU vitamin A, 3 IU vitamin E.

In still another embodiment, a composition of the invention is provided comprising, when present in an 8 oz. volume, 50 mg milk thistle extract, 50 mg ginseng extract, 50 mg ginger root extract, 25 mg fructose, 110 mg sodium chloride, 30 mg monopotassium phosphate, 30 mg magnesium sulfate, 50 mg cysteine, 25 mg glutamine, 2.1 µg vitamin B12, 0.7 mg vitamin B6, 3.5 mg vitamin B5, 0.525 mg vitamin B1, 7 mg vitamin B3, 0.6 mg vitamin B2, 60 mg vitamin C, 500 IU vitamin A, 3 IU vitamin E.

In various aspects, formulations include 7.2 oz. demineralized water and 0.75 oz. high fructose corn syrup (HFCS). In one aspect, the HFCS is HFCS-55. In another aspect, the HFCS is HFCS-42.

One of skill in the art will appreciate that the various components disclosed herein may be present in various combinations, and that not all of the disclosed components are present in every embodiment of the compositions provided herein.

The present invention also provides methods of treating hangover symptoms comprising administering to a subject in need of treating hangover symptoms an effective amount of any of the aforementioned compositions.

The present invention also provides the use of a composition of any of the afromentioned compositions in the manufacture of a medicament for the treatment of hangover symptoms.

DETAILED DESCRIPTION OF THE INVENTION

The present invention relates to compositions and methods for treating hangover symptoms. The composition comprises at least two different components selected from the group consisting of milk thistle extract, ginseng extract and ginger root extract.

The extract of the milk thistle plant, *Silybum marianum*, which belongs to the aster family (Asteraceae or Compositae), comprises silymarin as the active constituent. Silymarin consists of a mixture of three bioflavinoids (flavonolignans), silybin, silydianin, and silychristine, found in the fruit, seeds, and leaves of the milk thistle plant. Silybin is the main component of silymarin, amounting to 60-70% by weight, and is thought to have the most biological activity.

Historically, milk thistle extract has been used to treat disorders of the spleen, liver and gall bladder. Silymarin has been shown to have utility in many liver disorders including hepatitis, alcoholic liver disease, and hepatitis. It has also been shown to be useful for the treatment of toxin-induced liver toxicity including poisoning from death cap mushroom (*Amanita phalloides*). The mechanism of action for the beneficial effects of silymarin in liver disease is unknown, although antioxidant activity is a leading theory. In the animal model of cirrhosis produced by bile duct obliteration, silymarin has an antifibrotic effect.

Compositions are provided including milk thistle extract. In one aspect, the milk thistle extract, when present in an 8 oz. volume, is included in an amount ranging from about 2 mg to about 2 g. In other aspects, the milk thistle extract when present in an 8 oz. volume, is included in amounts of about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, about 1 g, about 1.1 g, about 1.2 g, about 1.3 g, about 1.4 g, about 1.5 g, about 1.6 g, about 1.7 g, about 1.8 g, about 1.9 g, or about 2 g.

Ginseng, another component of the claimed invention, is the name given to the dried roots of the ginseng plants (genus *Panax*) and, more particularly, to extracts of those roots. The roots and their extracts contain a variety of substances including saponins and sapogenins.

Ginseng has been extensively used, mostly in Asia, as a tonic to promote health and well being, and as a medicine in the treatment of various disease conditions. The beneficial attributes of ginseng are attributed to its saponin content, a mixture of dammarane triterpene glucosides referred to collectively as ginsenosides. Some ginsenosides have been isolated, and their structure determined. Such ginsenosides include Rb1, Rb2, Rc, Rd, Re, Rf and Rg (see U.S. Pat. No. 4,157,894).

There are three main species of ginseng, Oriental, Siberian and American. Oriental ginseng has been used in traditional Chinese medicine for thousands of years. Native Americans have likewise used American ginseng for all of their recorded history.

While all three forms share many common elements, there are differences among them. Siberian ginseng is not truly ginseng at all, but rather a distant cousin to the Oriental species. The stems, leaves, and roots of *Panax* species contain biologically active saponin glycosides, such as ginsenoside and panaxoside, as well as sugars, starch, mucilage, and a volatile oil. Most of the ginsenoside is located in the cambium.

Ginseng is held in high esteem because of its use as a medicinal plant. All forms of ginseng are said to aid in reducing stress, improving vitality and boosting the immune system. As a medicinal plant, ginseng seems was used as a remedy for all ailments, including depression, diabetes, fatigue, aging, inflammations, internal degeneration, nausea, tumors, pulmonary problems, dyspepsia, vomiting, nervousness, stress and ulcers. It has also been used to increase the appetite and bodily energy, regulate menses, ease childbirth, increase fertility of women and treat periodontal disease. Some consider it an aphrodisiac, stimulant, stomachic, and demulcent.

Compositions comprising ginseng are provided. In one aspect, the ginseng extract, when present in an 8 oz. volume, is included in an amount ranging from about 2 mg to about 2 g. In other aspects, the ginseng extract when present in an 8 oz. volume, is included in amounts of about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, about 1 g, about 1.1 g, about 1.2 g, about 1.3 g, about 1.4 g, about 1.5 g, about 1.6 g, about 1.7 g, about 1.8 g, about 1.9 g, or about 2 g.

Ginger root extract, yet another component of the composition described herein, is derived from the root of the herb *Zingiber officionale*, which grows widely in southwest India. Ginger is a popular spice in Indian cooking, and its medicinal uses have been well documented. As such, ginger root offers many benefits. Historically, ginger root has been used to ease menstrual cramps, treat seasickness and food poisoning, and to eliminate body odor. It is now one of the most popular herbal remedies for nausea, morning sickness and digestive problems.

Compositions comprising ginger root extract are provided. In one aspect, the ginger root extract, when present in an 8 oz. volume, is included in an amount ranging from about 2 mg to about 2 g. In other aspects, the ginger root extract, when present in an 8 oz. volume, is included in amounts of about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, about 1 g, about 1.1 g, about 1.2 g, about 1.3 g, about 1.4 g, about 1.5 g, about 1.6 g, about 1.7 g, about 1.8 g, about 1.9 g, or about 2 g.

Electrolytes

Dehydration is considered as one of the symptoms associated with a hangover or overindulging in alcohol consumption. Accordingly, the inclusion of electrolytes in the various aspects of the compositions of the invention is contemplated. Exemplary electrolytes include salts of a metal of the groups I and II of the periodic table, preferably the inorganic and organic salts of sodium, potassium, calcium and/or magnesium. Examples of such salts include, but are not limited to, are sodium acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulphate (anhydrous), sodium sulphate (Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulfate. In one aspect, the electrolytes are sodium chloride, monopotassium phosphate and magnesium sulfate and, when present in an 8 oz. volume, are included in amounts of about 50 mg to about 500 mg, from about 10 mg to about 200 mg and from about 10 mg to about 200 mg, respectively. In other aspects, sodium chloride, when present in an 8 oz. volume, is included in an amount ranging from about 50 mg, about 51 mg, about 52 mg, about 53 mg, about 54 mg, about 55 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, and about 500 mg, and magnesium sulfate and monopotossium phosphate, when present in an 8 oz. volume, are included in amounts of 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, and about 200 mg. In still another aspect, sodium chloride, magnesium sulfate and monopotassium phosphate, when in an 8 oz. volume, are present in amounts of 110 mg, 30 mg and 30 mg, respectively.

Vitamins

Vitamins are depleted during alcohol consumption. Thus, it is contemplated to include such nutrients (e.g., vitamin and vitamin supplements) into various aspects of the compositions of the invention.

Vitamin A helps in the formation and maintenance of healthy teeth, skeletal and soft tissue, mucous membranes, and skin. It is also known as retinol because it generates the pigments that are necessary for the working of the retina. It promotes good vision, especially in dim light. Beta-carotene is a precursor to vitamin A that has antioxidant properties, helping the body deal with unstable chemicals called free radicals.

Thiamine (B-1) helps the body cells convert carbohydrates into energy. It is also essential for the functioning of the heart and for healthy nerve cells, including those in the brain. Riboflavin (B-2) works with the other B vitamins and is important for body growth and red blood cell production. Similar to thiamine, it helps in releasing energy from carbohydrates. Niacin (B-3) is a B vitamin that helps maintain healthy skin and nerves. It is also important for the conversion of food to energy and may have cholesterol-lowering effects. Vitamin B-6 is also known as pyridoxine and aids in the formation of red blood cells and in the maintenance of normal brain function. It also assists in the synthesizing of antibodies in the immune system. Vitamin B-12, like the other B vitamins, is important for metabolism, participating in, for example, the formation of red blood cells. Pantothenic acid is essential for the metabolism of food. It is also essential in the synthesis of hormones and cholesterol. Biotin is essential for the metabolism of proteins and carbohydrates, and in the synthesis of hormones and cholesterol. Folate (folic acid) works with vitamin B-12 in the production of red blood cells and is necessary for the synthesis of DNA.

Vitamin C, also called ascorbic acid, promotes healthy teeth and gums, helps in the absorption of iron, and helps maintain normal connective tissue. It also promotes wound healing and is an antioxidant.

Vitamin D promotes the body's absorption of calcium, which is essential for the normal development and maintenance of healthy teeth and bones. It also helps maintain adequate blood levels of calcium and phosphorus, which are minerals necessary for many functions.

Vitamin E is also known as tocopherol and is an antioxidant. It is also important in the formation of red blood cells and the use of vitamin K.

Therefore, it is desirable to incorporate various vitamin types into the various aspects of the compositions of the invention. In one embodiment, vitamin B1 (thiamin) when present in an 8 oz. volume, is included in an amount ranging from about 0.1 mg to about 5 mg; vitamin B2 (riboflavin), when present in an 8 oz. volume, is included in an amount ranging from about 0.1 mg to about 5 mg; vitamin B3 (niacin), when present in an 8 oz. volume, is included in an amount ranging from about 1 mg to about 50 mg; vitamin B5 (pantothenoic acid), when present in an 8 oz. volume, is included in an amount ranging from about 1 mg to about 50 mg; vitamin B6, when present in an 8 oz. volume, is included in an amount ranging from about 0.1 mg to about 5 mg; and vitamin B12, when present in an 8 oz. volume, is included in an amount ranging from about 1 µg to about 50 µg. In one embodiment, vitamins B1, B2 and B6, when present in an 8 oz. volume, are included in amounts of about 0.1 mg, about 0.2 mg, about 0.3 mg, about 0.4 mg, about 0.5 mg, about 0.6 mg, about 0.7 mg, about 0.8 mg, about 0.9 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 3 mg, or about 4 mg, about 5 mg; vitamins B3 and B5, when present in an 8 oz. volume, are included in amounts of 1 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, or about 50 mg; and vitamin B12, when present in an 8 oz. volume, is included in amounts of 1 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 30 µg, about 40 µg, or about 50 µg.

In yet another embodiment, a composition of the invention provided further comprising vitamin A, when present in an 8 oz. volume, is included in an amount ranging from about 50 IU to about 1000 IU. In one aspect, vitamin A, when present in an 8 oz. volume, is included in amounts of about 50 IU, about 51 IU, about 52 IU, about 53 IU, about 54 IU, about 55 IU, about 55 IU, about 56 IU, about 57 IU, about 58 IU, about 59 IU, about 60 IU, about 61 IU, about 62 IU, about 63 IU, about 64 IU, about 65 IU, about 66 IU, about 67 IU, about 68 IU, about 69 IU, about 70 IU, about 71 IU, about 72 IU, about 73 IU, about 74 IU, about 75 IU, about 76 IU, about 77 IU, about 78 IU, about 79 IU, about 80 IU, about 81 IU, about 82 IU, about 83 IU, about 84 IU, about 85 IU, about 86 IU, about 87 IU, about 88 IU, about 89 IU, about 90 IU, about 91 IU, about 92 IU, about 93 IU, about 94 IU, about 95 IU, about 96 IU, about 97 IU, about 98 IU, about 99 IU, about 100 IU, about 200 IU, about 300 IU, about 400 IU, about 500 IU, about 600 IU, about 700 IU, about 800 IU, about 900 IU and 1000 IU.

In another embodiment, a composition of the invention is provided further comprising, vitamin C, when present in an 8 oz. volume, is included in an amount ranging from about 10 mg to about 100 mg. In aspect, vitamin C, when present in an 8 oz. volume, is included in amounts of 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg.

In yet another embodiment, a composition of the invention is provided further comprising vitamin E, when present in an 8 oz. volume, is included in an amount ranging from about 1 IU to about 50 IU. In aspect, vitamin E, when present in an 8 oz. volume, is included in amounts of about 1 IU, about 3 IU, about 4 IU, about 5 IU, about 6 IU, about 7 IU, about 8 IU, about 9 IU, about 10 IU, about 11 IU, about 12 IU, about 13 IU, about 14 IU, about 15 IU, about 16 IU, about 17 IU, about 18 IU, about 19 IU, about 20 IU, about 30 IU, about 40 IU, or about 50 IU.

Amino Acids

Including one or more amino acids into the compositions of the invention to offset alcohol's effect is contemplated. Therefore, in one embodiment, the aforementioned composition is provided further comprising one or more amino acids selected from the group consisting of alanine, arginine, creatine, cysteine, glysine, histidine, glutamine, lysine, methionine, ornithine, leucine, isoleucine, serine, tyrosine, asparagine, aspartic acid, threonine, proline, tryptophan, valine, and phenylalanine.

Alcohol consumption inhibits glutamine production, one of the body's natural stimulants. Therefore, in response to the inhibition, the body overproduces glutamine. Severe glutamine rebound during a hangover also may be responsible for tremors, anxiety, restlessness and increased blood pressure.

For example, glutamine, when present in an 8 oz. volume, is included in an amount ranging from about 5 mg to about 100 mg or in amounts of about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, and about 100 mg.

It has been reported that cysteine can help the body metabolize alcohol. Accordingly, inclusion of cysteine in a composition of the invention is contemplated. For example, cysteine, when present in an 8 oz. volume, is included in an amount ranging from about 10 mg to about 100 mg or in amounts of about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, and about 100 mg.

Carbohydrates

Several alterations in the metabolic state of the liver and other organs occur in response to the presence of alcohol in the body and can result in low blood sugar levels (i.e., low glucose levels, or hypoglycemia). Alcohol metabolism leads to fatty liver and a buildup of an intermediate metabolic product, lactic acid, in body fluids (i.e., lactic acidosis). Both of these effects can inhibit glucose production. Because glucose is the primary energy source of the brain, hypoglycemia can contribute to hangover symptoms such as fatigue, weakness, and mood disturbances. Therefore, including a carbohydrate source in the composition of the invention is contemplated. Exemplary carbohydrates include, but are not limited to, monosaccharides, a disaccharides, oligosaccharides and a glucose polymers. Modified carbohydrates, such as sucrolose, are also contemplated.

In one aspect, the formulation include high fructose corn syrup, which when present in an 8 oz. volume, is provided at about 0.6 oz., about 0.61 oz., about 0.62 oz., about 0.63 oz., about 0.64 oz., about 0.65 oz., about 0.66 oz., about 0.67 oz., about 0.68 oz., about 0.69 oz., about 0.70 oz., about 0.71 oz., about 0.72 oz., about 0.73 oz., about 0.74 oz., about 0.75 oz., about 0.76 oz., about 0.77 oz., about 0.78 oz., about 0.79 oz., about 0.80 oz., about 0.81 oz., about 0.82 oz., about 0.83 oz., about 0.84 oz., or about 0.85 oz.

In another aspect, carbohydrate of the formulation is derived from citric acid.

Flavoring Agents

One or more flavoring agents may be added to the compositions of the invention in order to enhance their palatability. Any natural or synthetic flavor agent can be used in the present invention. For example, one or more botanical and/or fruit flavors may be utilized herein. As used herein, such flavors may be synthetic or natural flavors.

Exemplary fruit flavors include exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, grapefruit flavors, and the like. These fruit flavors can be derived from natural sources such as fruit juices and flavor oils, or may alternatively be synthetically prepared.

Exemplary botanical flavors include, for example, tea (e.g., black and green tea), aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardimom, nutmeg, cassia bark, buchu, cinnamon, jasmine, haw, chrysanthemum, water chestnut, sugar cane, lychee, bamboo shoots, vanilla, coffee, and the like.

The flavor agent can also comprise a blend of various flavors. If desired, the flavor in the flavoring agent may be formed into emulsion droplets which are then dispersed in the beverage composition or concentrate. Because these droplets usually have a specific gravity less than that of water and would therefore form a separate phase, weighting agents (which can also act as clouding agents) can be used to keep the emulsion droplets dispersed in the beverage composition or concentrate. Examples of such weighting agents are brominated vegetable oils (BVO) and resin esters, in particular the ester gums. See L. F. Green, Developments in Soft Drinks Technology, Vol. 1, Applied Science Publishers Ltd., pp. 87-93 (1978) for a further description of the use of weighting and clouding agents in liquid beverages. Typically the flavoring agents are conventionally available as concentrates or extracts or in the form of synthetically produced flavoring esters, alcohols, aldehydes, terpenes, sesquiterpenes, and the like.

The amount of flavor agent used will vary, depending on the agents used and the intensity desired in the finished product. The amount can be readily determined by one skilled in the art. Generally, if utilized, the flavor agent should be present at a level of from about 0.0001% to about 0.5%.

Flavanols

Flavanols are natural substances present in a variety of plants (e.g., fruits, vegetables, and flowers). The flavanols which may be utilized in the present invention can be extracted from, for example, fruit, vegetables, green tea or other natural sources by any suitable method well known to those skilled in the art. Flavanols may be extracted from either a single plant or mixtures of plants. Plants containing flavanols are known to those skilled in the art.

The amount of flavanols in the various aspect of the compositions of the invention can vary. However, wherein one or more flavanols are utilized, preferably from about 0.001% to about 5% by weight of the composition.

Coloring Agent

Small amounts of one or more coloring agents may be utilized in the compositions of the present invention. FD&C dyes (e.g., yellow #5, blue #2, red #40) and/or FD&C lakes are preferably used. By adding the lakes to the other powdered ingredients, all the particles, in particular the colored iron compound, are completely and uniformly colored and a uniformly colored beverage mix is attained. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and b-carotene may also be used. Additionally, other natural coloring agents may be utilized including, for example, fruit, vegetable, and/or plant extracts such as grape, black currant, aronia, carrot, beetroot, red cabbage, and hibiscus.

The amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the composition.

Preservatives

Preservatives may or may not be needed for use in the present compositions. Techniques such as aseptic and/or clean-fill processing may be utilized to avoid preservatives. One or more preservatives may, however, optionally be added to the present compositions. Preferred preservatives include, for example, sorbate, benzoate, and polyphosphate preservatives (for example, sodium hexametapolyphosphate).

Preferably, wherein a preservative is utilized herein, one or more sorbate or benzoate preservatives (or mixtures thereof) are utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof.

Wherein a composition comprises a preservative, the preservative is preferably included at levels from about 0.0005% to about 0.5%, more preferably from about 0.001% to about 0.4% of the preservative, still more preferably from about 0.001% to about 0.1%, even more preferably from about 0.001% to about 0.05%, and most preferably from about 0.003% to about 0.03% of the preservative, by weight of the composition. Wherein the composition comprises a mixture of one or more preservatives, the total concentration of such preservatives is preferably maintained within these ranges.

Acidulants

If desired, the present compositions may optionally comprise one or more acidulants. An amount of an acidulant may be used to maintain the pH of the composition. Compositions of the present invention, in various aspects, have a pH of from about 2 to about 9, from about 2.5 to about 8.5, from about 3 to about 8, from about 03.5 to about 7.5, from about 4 to about 7, from about 4.5 to about 6.5, or from about 5 to about 6.

Beverage acidity can be adjusted to and maintained within the requisite range by known and conventional methods, e.g., the use of one or more of the aforementioned acidulants. Typically, acidity within the above recited ranges is a balance between maximum acidity for microbial inhibition and optimum acidity for the desired beverage flavor.

Organic as well as inorganic edible acids may be used to adjust the pH of the beverage, and may be added additional to the acid serving as part of the second component herein. The acids can be present in their undissociated form or, alternatively, as their respective salts, for example, potassium or sodium hydrogen phosphate, potassium or sodium dihydrogen phosphate salts. The preferred acids are edible organic acids which include citric acid, malic acid, fumaric acid, adipic acid, phosphoric acid, gluconic acid, tartaric acid, ascorbic acid, acetic acid, phosphoric acid or mixtures thereof. The most preferred acids are citric and malic acids.

The acidulant can also serve as an antioxidant to stabilize beverage components. Examples of commonly used antioxidant include but are not limited to ascorbic acid, EDTA (ethylenediaminetetraacetic acid), and salts thereof.

The amount of acidulant used will vary, depending on the agent used and the pH desired in the finished product. The amount can be readily determined by one skilled in the art. Generally, if utilized, the acidulant should be present at a level of from about 0.0001% to about 0.5% by weight of composition.

Water

The compositions of the invention may comprise from 0% to about 99.999% water, by weight of the composition. The compositions may comprise at least about 4% water, at least about 20% water, at least about 40% water, at least about 50% water, at least about 75% water, and at least about 80% water. The water included at these levels includes all added water and any water present in combination components, for example, fruit juice.

In various embodiments, the composition includes, in an 8 oz volume, about 6.0 oz., about 6.1 oz, about 6.2 oz., about 6.3 oz, about 6.4 oz., about 6.5 oz, about 6.6 oz., about 6.7 oz, about 6.8 oz., about 6.9 oz, about 7.0 oz., about 7.1 oz, about 7.2 oz., about 7.3 oz, about 7.4 oz., about 7.5 oz, about 7.6 oz., about 7.7 oz, about 7.8 oz., about 7.9 oz, and about 8.0 oz. of water. In one aspect, the water component of the formulation is demineralized water.

Carbonation Component

Carbon dioxide is optionally introduced into the water which is mixed with a composition of the invention to achieve carbonation. The carbonated beverage can be placed into a container, such as a bottle or can, and then sealed. Any conventional carbonation methodology may be utilized to make carbonated beverage compositions of this invention. The amount of carbon dioxide introduced into the beverage will depend upon the particular flavor system utilized and the amount of carbonation desired.

Administration

Optimum effects of the composition of the invention in reducing or preventing the onset of the deleterious effects associated with alcohol ingestion includes self-administration of one dose of the composition of the invention in intervals of one to three hours during moderate alcohol consumption or one to two hours during heavy drinking.

The formulation is to be consumed in an amount based on the amount of alcohol consumed and body type of the consumer. The consumer will appreciate that one or more amounts can be consumed over a period of time until a desired result is achieved. The formulation can be consumed while before consuming alcohol, while consuming alcohol, and/or after consuming alcohol in one ore more amounts. In various aspects, the formulation is consumed prior to going to sleep after drinking and upon awakening from sleep.

It is highly desirable to administer one or few final doses of the composition of the invention at the end of the period of alcohol consumption.

The methods of the present invention may be used as a prophylactic or therapeutic treatment.

What is claimed is:

1. A composition in oral dosage form for the relief of hangover symptoms comprising:
   (a) milk thistle extract, ginseng extract and ginger root extract, wherein the milk thistle extract, ginseng extract and ginger root extract are each present in an amounts ranging from about 2 mg to about 2 g;
   (b) an electrolyte selected from the group consisting of acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulphate (anhydrous), sodium sulphate (Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulfate, and monopotassium phosphate, wherein the electrolyte is present in an amount ranging from about 10 mg to about 500 mg;
   (c) a carbohydrate selected from the group consisting of a monosaccharide, a modified carbohydrate, an oligosaccharide, a glucose polymer, and fructose;
   (d) vitamin B1 (thiamin) in an amount ranging from about 0.1 mg to about 5 mg, vitamin B2 (riboflavin) in an amount ranging from about 0.1 mg to about 5 mg, vitamin B3 (niacin) in an amount ranging from about 1 mg to about 50 mg, vitamin B5 (pantothenoic acid) in an amount ranging from about 1 mg to about 50 mg, vitamin B6 in an amount ranging from about 0.1 mg to about 5 mg, and vitamin B12 in an amount ranging from about 1 µg to about 50 µg;
   (e) vitamin A, in an amount ranging from about 50 IU to about 1000 IU;
   (f) vitamin C in an amount ranging from about 10 mg to about 100 mg;
   (g) vitamin E in an amount ranging from about 1 IU to about 50 IU; and
   (h) an amino acid selected from the group consisting of cysteine and glutamine, wherein the amino acid is present in an amount ranging from 10 mg to about 100 mg.

2. The composition of claim 1, wherein the composition is an aqueous composition.

3. A composition in oral dosage form for the relief of hangover symptoms comprising 50 mg milk thistle extract, 50 mg ginseng extract, 50 mg ginger root extract, 25 mg fructose, 110 mg sodium chloride, 30 mg monopotassium phosphate, 30 mg magnesium sulfate, 50 mg cysteine, 2.1 µg vitamin B12, 0.7 mg vitamin B6, 3.5 mg vitamin B5, 0.525 mg vitamin B1, 7 mg vitamin B3, 0.6 mg vitamin B2, 60 mg vitamin C, 500 IU vitamin A and 3 IU vitamin E.

* * * * *